US006509915B2

(12) United States Patent
Berman et al.

(10) Patent No.: US 6,509,915 B2
(45) Date of Patent: *Jan. 21, 2003

(54) SYSTEMS AND METHODS FOR DIRECT IMAGE MANIPULATION

(75) Inventors: Phillip Berman, Tucson, AZ (US); Henky Wibowo, Tucson, AZ (US)

(73) Assignee: Eastman Kodak Company, Rochester, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/892,315

(22) Filed: Jun. 26, 2001

(65) Prior Publication Data

US 2002/0054172 A1 May 9, 2002

Related U.S. Application Data

(62) Division of application No. 08/965,819, filed on Oct. 7, 1997, now Pat. No. 6,448,956
(60) Provisional application No. 60/064,436, filed on Oct. 31, 1997.

(51) Int. Cl.⁷ .............................................. G06F 13/00
(52) U.S. Cl. ........................ 345/840; 345/156; 345/856
(58) Field of Search ................................ 345/156, 157, 345/158, 161, 162, 163, 835, 810, 840, 781, 788, 803, 747, 856

(56) References Cited

U.S. PATENT DOCUMENTS

| | | |
|---|---|---|
| 4,586,035 A | 4/1986 | Baker et al. |
| 4,975,690 A | 12/1990 | Torres |
| 5,146,556 A | 9/1992 | Hullot et al. |
| 5,416,900 A | 5/1995 | Blanchard et al. |
| 5,552,806 A | 9/1996 | Lenchik |
| 5,568,603 A | 10/1996 | Chen et al. |
| 5,572,648 A | 11/1996 | Bibayan |
| 5,581,670 A | 12/1996 | Bier et al. |
| 5,590,265 A | 12/1996 | Nakazawa |
| 5,602,997 A | 2/1997 | Carpenter et al. |
| 5,617,114 A | 4/1997 | Bier et al. |
| 5,659,338 A * | 8/1997 | Nakasuji et al. ............ 345/201 |
| 5,710,897 A | 1/1998 | Schneider |
| 5,757,371 A | 5/1998 | Oran et al. |
| 5,767,850 A | 6/1998 | Ramanathan et al. |
| 5,796,402 A | 8/1998 | Ellison-Taylor |
| 5,796,403 A | 8/1998 | Adams et al. |
| 5,799,292 A * | 8/1998 | Hekmatpour ............... 345/797 |
| 5,923,307 A * | 7/1999 | Hogle, IV ................... 345/840 |
| 5,929,854 A | 7/1999 | Ross |

OTHER PUBLICATIONS

Reference Guide for Image Search & Retrieval (IS&R) Computer–Based Training Jul. 11, 1997.*
Microsoft Office 6–in–1; Townsend et al., 1995.*

(List continued on next page.)

*Primary Examiner*—Cao H. Nguyen

(57) ABSTRACT

An image manipulation system including: at least one of a plurality of display monitors for displaying at least one of a plurality of digital images, each of the display monitors including at least one of a plurality of image display windows, wherein each of the image display windows is capable of displaying at least one of the digital images. The system further includes a cursor and instructions associated with virtual spaces of the image display windows, and is capable of designating the virtual spaces of each of the image display windows as function activating; generating the instructions associated with the virtual spaces; assigning each of the virtual spaces with image manipulation functions corresponding to a position of the cursor when located within each of the virtual spaces; and executing the instructions associated with each of the virtual spaces.

1 Claim, 15 Drawing Sheets

OTHER PUBLICATIONS

Mastering Windows 3.1; Robert Coward, 1992.*
Cowart, Mastering Windows 3.1 (Special Edition), Sybex Corp. 5–6, 10–18, 63–68, 235–237, 253–255, 593–596, 1992.

Refernce Guide for Image Search and Retreival for U.S. Dep. of Commerce, USPTO, Jul. 11, 1997.
Microsoft Office, 6–in–1, Townsend et al., Que, pp. 113–122; 233–235; 252–257, 1995.

* cited by examiner

Image Display in Dual-Monitor Mode

Seven-Stack Display

Four-Stack Display

SYSTEMS AND METHODS FOR DIRECT IMAGE MANIPULATION

CROSS REFERENCE TO RELATED APPLICATION

This application is a divisional of U.S. application Ser. No. 08/965,819 filed Oct. 7, 1997, now U.S. Pat. No. 6,448,956 which claims priority from U.S. Provisional Application Serial No. 60/064,436 filed Oct. 31, 1997, for subject matter common thereto.

FIELD OF THE INVENTION

The present invention relates to systems and methods for directly manipulating digital images on image display monitors. More particularly, the present invention relates to systems and methods that allow image manipulation without using conventional toolbars or menubars for controlling the various manipulation functions, but in which the displayed digital image itself is mapped into virtual spaces corresponding to image manipulation functions that can be executed via the pointing device.

BACKGROUND OF THE INVENTION

Conventional image manipulation systems and graphical user interfaces ("GUFs") use a cooperation between screen representations, such as portrayed buttons, menu items or icons, and a cursor controlled by, for example, a mouse. These conventional systems and methods require toolbars, menubars and other displays that intrude on the displayed image and use cumbersome and time-consuming steps for executing desired image manipulation functions.

The interposition of such tools and techniques stands in the way of a more natural and intuitive approach to image manipulation.

In addition, the continuous presence of conventional toolbars or other images dedicated to control of the image can cause undesirable "bum-in" of high luminescence display screens. Conventional toolbars and menubars can also increase the level of background light emitted by the display and related GUI, thereby degrading the quality of the displayed images.

Consequently, a need exists for direct image manipulation systems and GUI's that do not utilize conventional intrusive toolbars, menubars and other conventional display capabilities. The need is especially great in the medical field, where for example, radiologists traditionally use light boxes to view x-ray prints, MRI images and other medical images. By avoiding the use of conventional display capabilities and providing a more natural and intuitive approach to image manipulation, a radiologist could manipulate digital images on an image display just as easily as he or she could handle "hard" prints in front of a light box, and in a manner quite similar.

The need for direct image manipulation capabilities is also great in the field of teleradiology, where direct image manipulation systems are required for use over local area and wide area computer networks. Such a system would allow physicians or radiologists, for example, to access and review medical images from a remote site with the same convenience and reliability as they would in the office or hospital radiology department. A physician or radiologist could thereby provide around-the-clock coverage from a remote site without delays or midnight drives to the hospital. Immediate remote access would benefit emergency patients by enabling a fast, expert access to images essential to accurate diagnosis and treatment. This, coupled with improved, more natural image manipulation arrangements would significantly enhance the physician's or radiologist's ability to serve the needs of the patient.

In the field of teleradiology, there is also a need for manipulation systems that are compatible with the Digital Imaging and Communications in Medicine ("DICOM") standard. The DICOM standard defines formatting, storage and transmission protocols for digital images used by the medical community. These protocols allow medical images and associated clinical information to be captured, transferred, viewed and manipulated with DICOM-compatible hardware and software.

Therefore, a principle object of the present invention is to provide a system and method for direct manipulation of digital images that do not rely on conventional portrayed items such as toolbars or menubars for controlling various image manipulation functions.

Another object of the present invention is to provide a system and method for direct manipulation of digital images that utilize, when required, non-intrusive means for displaying and activating image manipulation functions and tools.

Still another object of the present invention is to provide a system for direct manipulation of digital images that is adaptable for use in local area and wide networks.

Yet another object of the present invention is to provide a system for direct manipulation of digital images that is particularly adaptable for teleradiology applications.

Yet another object of the present invention is to provide a system for direct manipulation of digital images that is DICOM-compatible.

Yet another object of the present invention is to provide a computer program implementing systems of image manipulation pursuant to the foregoing objects of the invention.

SUMMARY OF THE INVENTION

The present invention relates to systems and methods for direct manipulation of digital images via a pointing device such as a mouse but without reliance on conventional displayed image manipulation tools or icons. In accordance with a preferred embodiment of the present invention, a system for direct image manipulation includes: at least one display monitor for displaying at least one of a plurality of digital images, the display monitor including at least one of a plurality of image display windows, wherein each of the image display windows is capable of displaying at least one of the digital images. When a selected image display window is activated, the image manipulation system (1) designates virtual spaces as function executing by means of a cursor and instructions associated with the virtual spaces, (2) generates the instructions associated with the virtual spaces, (3) assigns each of the virtual spaces to image manipulation functions corresponding to a position of the cursor when located within each of the virtual spaces, and (4) executes the instructions associated with each of the virtual spaces.

In accordance with another preferred embodiment of the present invention, a system for direct image manipulation includes: means for directly manipulating digital images with a pointing device in a non-intrusive manner; a central repository for providing image data corresponding to the digital images; a central station for processing the image data and for viewing and manipulating the corresponding digital images; a first network connected to the central repository, the first network. Including at least one local site and at least one local node at the site for processing and for viewing and manipulating the digital images; and a second network connected to the central repository, the second network including at least one remote site and at least one remote node at the remote site for processing the image data and for viewing and manipulating the digital images.

In accordance with another preferred embodiment of the present invention, an image manipulation system for in-hospital teleradiology includes: means for directly manipulating digital images with a pointing device in a non-intrusive manner; a central repository for providing image data corresponding to the digital images; a central station for processing the image data and for viewing and manipulating the corresponding digital images; and a local network connected to the central repository, the local network including at least one local site and at least one local node at the local site for processing the image data and for viewing and manipulating the digital images.

In accordance with yet another preferred embodiment of the present invention, an image manipulation system for multi-site teleradiology includes: means for directly manipulating digital images with a pointing device in a non-intrusive manner; a central repository for providing image data corresponding to the digital images; a central station for processing the image data and for viewing and manipulating the digital images; and a network connected to the central repository, the network including at least one remote site and at least one remote node at the remote site for processing and for viewing and manipulating the digital images.

In accordance with another aspect of the present invention, a method for direct manipulation of digital images includes the steps of displaying at least one of a plurality of digital images on at least one display monitor, the display monitor including at least one of a plurality of image display windows, wherein each of the image display windows is capable of displaying at least one of the digital images; designating virtual spaces of each of the image display windows as function executing, the designating means including a cursor and instructions associated with the virtual spaces; generating the instructions associated with the virtual spaces; assigning each of the virtual spaces with a unique function corresponding to the position of the cursor when located within each of the virtual spaces; and executing the instructions associated with the virtual spaces.

In accordance with another aspect of the present invention, a method for direct manipulation of digital images includes the steps of selecting at least one of a plurality of digital images to be displayed; loading image data associated with the digital images into computer memory; initializing at least one of a plurality of image display windows for displaying the digital images; executing one of the image display windows; partitioning the activated image display window into a plurality of regions; assigning each of the regions to a set of instructions required for performing one of a plurality of image manipulation functions associated with each of the regions within the activated image window; executing a selected one of the image manipulation functions within the activated image display window, the executing step including the steps of moving a cursor into the region associated with the desired image manipulation function, and manually engaging instructions associated with the selected image manipulation function.

In accordance with another aspect of the present invention, a computer program product is provided for implementing a system for directly manipulating digital images with a pointing device. The computer program includes a computer usable medium and a computer readable program code embodied therein for: displaying at least one of a plurality of digital images on at least one display monitor, the display monitor comprising at least one of a plurality of image display windows, wherein each of the image display windows is capable of displaying at least one of the digital images; designating virtual spaces of each of the image display windows as function activating by way of a cursor and instructions associated with the virtual spaces; generating the instructions associated with the virtual spaces; assigning each of the virtual spaces with a unique function corresponding to a position of the cursor when located within each of the virtual spaces; and executing the instructions associated with each of the virtual spaces.

In accordance with yet another aspect of the present invention, a computer program for use with an image manipulation system includes a computer usable medium and a computer readable program code embodied in the computer usable medium. The computer readable program code further includes: an image data processing object class for processing image data; an image data interface object class for providing an interface between the image data and the computer readable program code, wherein the image data interface object class receives the image data and creates one or more image interface objects containing image bitmap data. The computer readable program code also includes: an image view object class for processing the image bitmap data and for displaying one or more images in one or more display areas; an image floating window object class for defining the display areas on one or more display monitors, the image floating window object class further including a user interface for executing image manipulation functions; an image child window object class for mapping the image interface objects to one or more image display windows within the display areas; an image display region object class for providing parameters associated with the image display areas and the image display windows, wherein the parameters are passed to the image view object class; a window/level object class for providing window and level data to the image view object class; and a coordinate mapping object class for generating mapping data between image coordinate spaces and image display window coordinate spaces, wherein mapping data is provided to the image floating window object class.

In accordance with still another aspect of the present invention, a method for manipulating digital images is provided wherein the method includes: creating one or more cursor handles corresponding to cursors to be used in image display windows; creating one or more function handles corresponding to virtual spaces of the image display windows; creating a table in computer memory for storing the cursor handles and function handles; storing the cursor and function handles in the table; storing dimension and position data associated with the virtual spaces in the table; detecting motion of a pointing device; checking the position of the pointing device; converting the position of the pointing device into an index of the table; switching the cursor to the cursor handle found in the table; and notifying a computer operating system that a new cursor handle has been created.

BRIEF DESCRIPTION OF THE DRAWINGS

For a complete understanding of the present invention and the advantages thereof, reference is now made to the following description taken in conjunction with the accompanying drawings in which like reference numbers indicate like features and wherein.

DETAILED DESCRIPTION OF THE INVENTION

Figure 1:
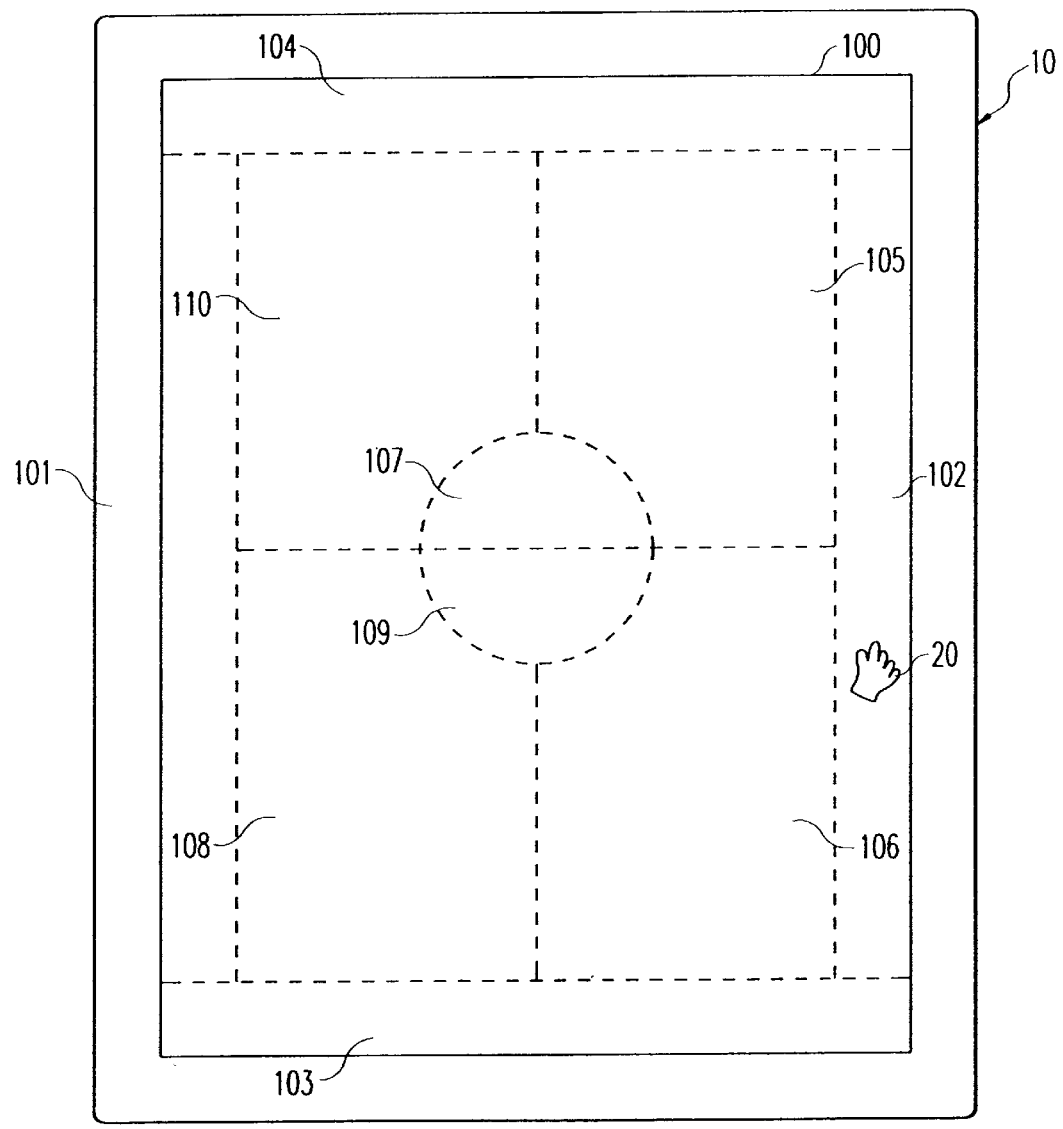
FIG. 1 is a front view of an image manipulation system according to a preferred embodiment of the present invention.

FIG. 1 shows an image manipulation system according to a preferred embodiment of the present invention. The image manipulation system 1 includes: at least one display monitor 10 for displaying at least one of a plurality of digital images, the display monitor 10 including at least one of a plurality of image display windows 100 (only one shown in FIG. 1), wherein each of the image display windows 100 is capable of displaying at least one of the digital images. When a selected image display window is activated, the image manipulation system 1 (1) designates virtual spaces 101 through 110 as function executing by means of a cursor 20 and instructions associated with the virtual spaces 101 through 110, (2) generates the instructions associated with the virtual spaces 101 through 110, (3) assigns each of the virtual spaces 101 through 110 with image manipulation functions corresponding to a position of the cursor 20 when located within each of the virtual spaces 101 through 110, (4) and executes the instructions associated with each of the virtual spaces 101 through 110.

The image manipulation system 1 as shown in FIG. 1 further includes a pointing device (not shown), such as a mouse, for generating the instructions associated with each of the virtual spaces 101 through 110. As the cursor 20 of the pointing device is moved through the image display window 100, the image display window 100 is activated and partitioned geographically into a plurality of virtual spaces 101 through 110. The number and arrangement of virtual spaces 101 through 110 in FIG. 1 are shown by way of example and not limitation. The virtual spaces 101 through 110 are in turn mapped to instructions or tools for performing image manipulation functions on the digital image or images displayed in the activated image display window 100. The image manipulation functions are then manually executed via means on the pointing device.

Referring again to FIG. 1, a preferred embodiment of present invention includes at least one active image display window 100 that is mapped into ten unique virtual spaces 101 through 110 representing unique manipulation functions or tools. As the cursor 20 of the pointing device changes position on the active image display window 100, the appearance of the cursor 20 changes in accordance with the manipulation function mapped to that space occupied by the cursor 20. The appearance of the cursor 20 serves to cue the user as to which manipulation function or tool is currently active.

The manipulation functions performed by the present invention can be categorized as basic image manipulation functions or specialized image manipulation functions. In a preferred embodiment of the present invention, for example, virtual spaces 101 through 104 are mapped to basic image manipulation functions, and virtual spaces 105 through 110 are mapped to specialized image manipulation functions. Basic image manipulation functions, for example, may include forward image scrolling, backward image scrolling, "dragging and dropping," etc. Specialized image manipulation functions, for example, may include image rotation, stacking, zooming, panning, etc.

Figure 2A:
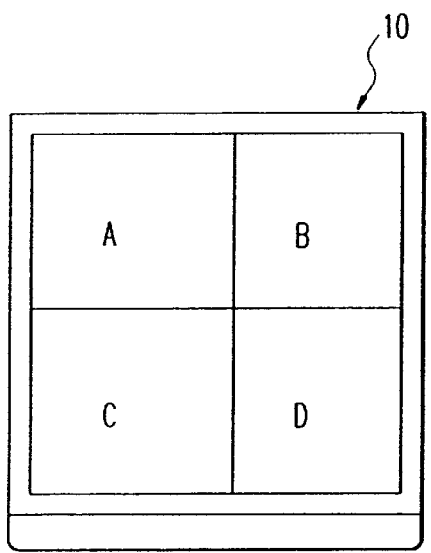
FIGS. 2A and 2B are illustrations of image display windows configured in stack and page display modes, respectively, according to a preferred embodiment of the present invention.
Figure 2B:
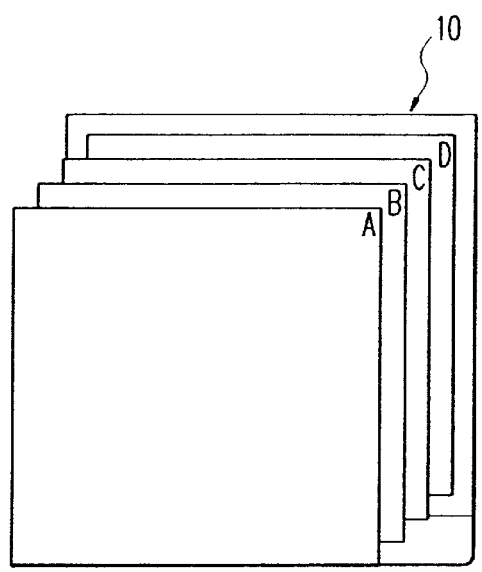

FIGS. 2A and 2B show the operation of the image display device 1 when a plurality of image windows A through D are displayed in the image display area of display monitor 10. The image windows A through D can be displayed in a page display mode as shown in FIG. 2A, or a stack display mode as shown in FIG. 2B. The number and arrangement of the image windows A through D in FIGS. 2A and 2B ate shown by way of example and not limitation.

In the page display mode, digital images are displayed in a conventional page layout as shown in FIG. 2A. The image windows A through D containing digital images A through D (not shown) are arranged such that: the first image, image A, lies in the upper left corner of the image display area; the second image, image B, lies to the right of image A; the third image, image C, lies beneath image A in the bottom left corner in a second row of the image display area; the fourth image, image D, lies in the second row to the right of image C; and so forth as required.

Alternatively, the digital images in a stack display mode are arranged such that the digital images A through D are arranged one on top of other as shown in FIG. 2B. The edges of the stacked digital images A through D in FIG. 2B are shown for illustration purposes and do not appear in the actual embodiments of the present invention. The image windows A through D are arranged such that: the first image, image A, lies on top of the second image, image B; image B lies on top of the third image, image C; image C lies on top of the fourth image, image D; and so forth depending upon the number of digital images in the stack. By advancing the digital images, the user can "shuffle" through the stack to display the desired image of the stack.

Figure 3A:
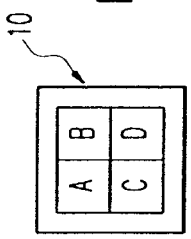
FIGS. 3A through 3C are illustrations of image manipulation systems configured with one, two and four display monitors, respectively, according to a preferred embodiment of the present invention.
Figure 3B:
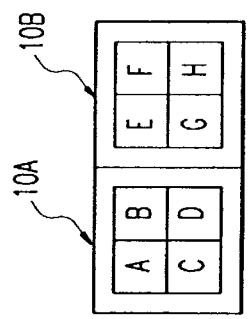
Figure 3C:
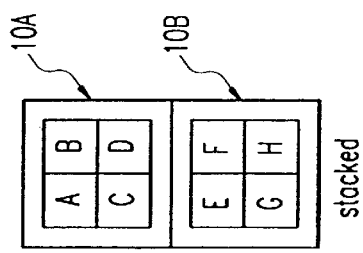
Figure 3C:
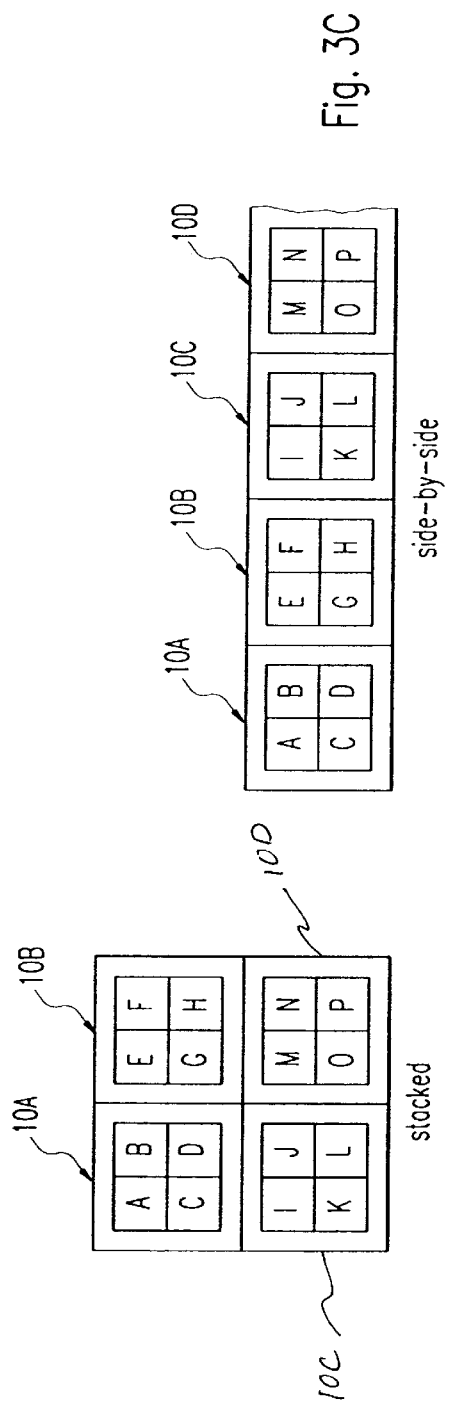

In either the stack display mode or page display mode, the stacks or pages of digital images can be displayed on a single display monitor 10, as shown in FIG. 3A, or on multiple display monitors 10A through 10D as shown in FIGS. 3B and 3C. The multiple display monitors 110A through 110D can be arranged in "side-by-side" or stacked" configurations. FIG. 3B for example shows "side-by-side" and "stacked" configurations for a two-monitor device displaying image display windows A through H. FIG. 3C shows similar configurations for a four-monitor device displaying image display windows A through P.

Figure 4:
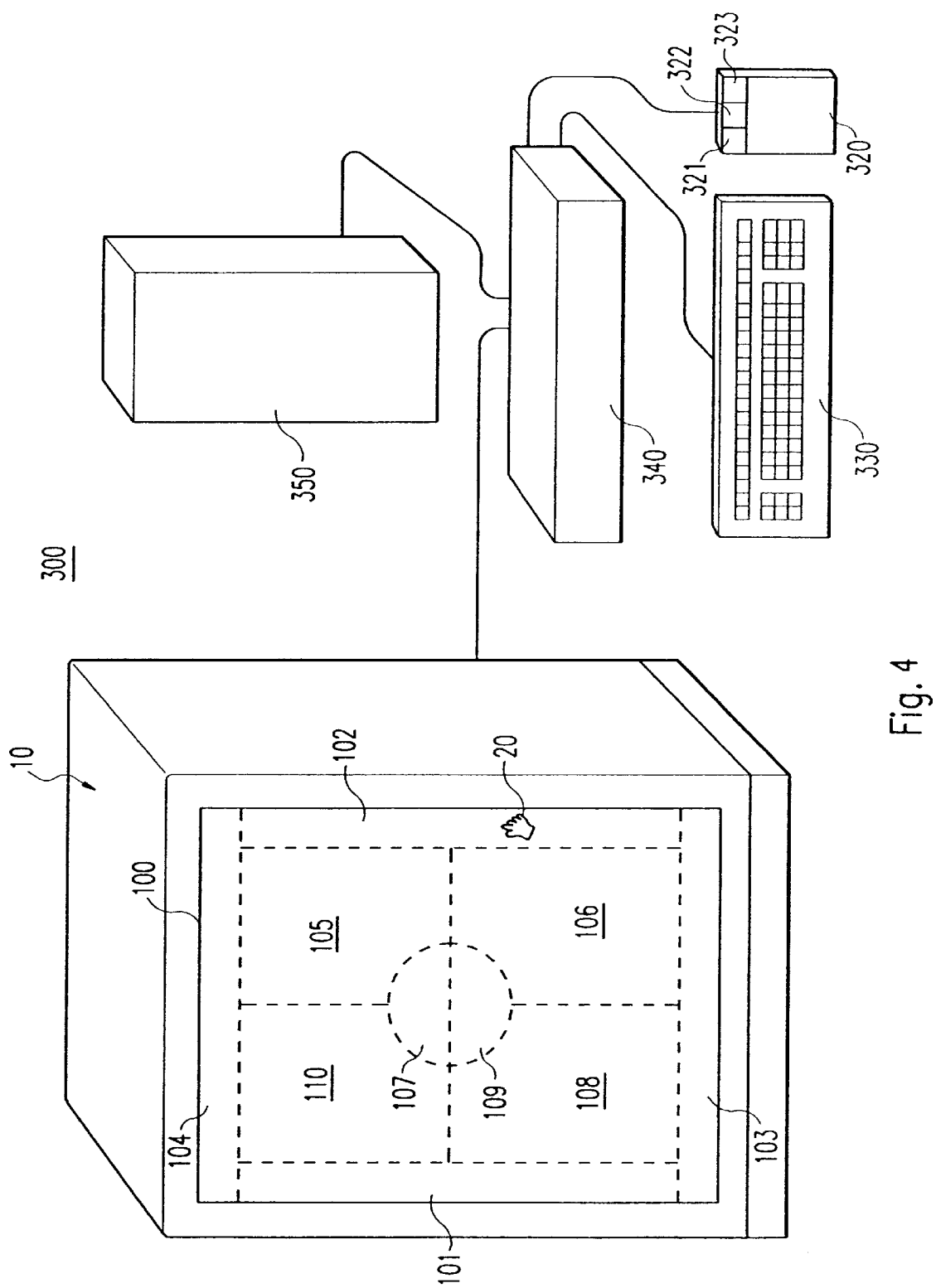
FIG. 4 is a diagram of an image manipulation system configured as a workstation according to a preferred embodiment of the present invention.

FIG. 4 shows a preferred embodiment of the present invention wherein a system for direct manipulation of digital images includes a workstation 300. The workstation 300 includes a display monitor 10, a mouse 320, a client processor 340, a keyboard 330 and server 350. Image data stored in the server 350 is provided to the client processor 340, which processes the image data for display at the display monitor 10. Alternatively, the image data or information maybe stored on a hard drive (not shown) connected the client processor 340. Mouse 320 is used for image manipulation and further includes a left mouse button 321, a center mouse button 322 and a right mouse button 323. The display monitor includes an image display window 100 that is activated when the cursor 20 lies within its boundaries.

When activated, the image display window 100 of FIG, 4 is partitioned into virtual spaces 101 through 110. The virtual spaces include: a left border region 101; a right border region 102; a bottom border region 103; a top border region 104; a window/level function region 105; a magnification/zoom/panning function region 106; a synch/unsynch function region 107; a rotation function region 108; a stack/unstack function region 109; and an image quantity function region 110.

Figure 12:
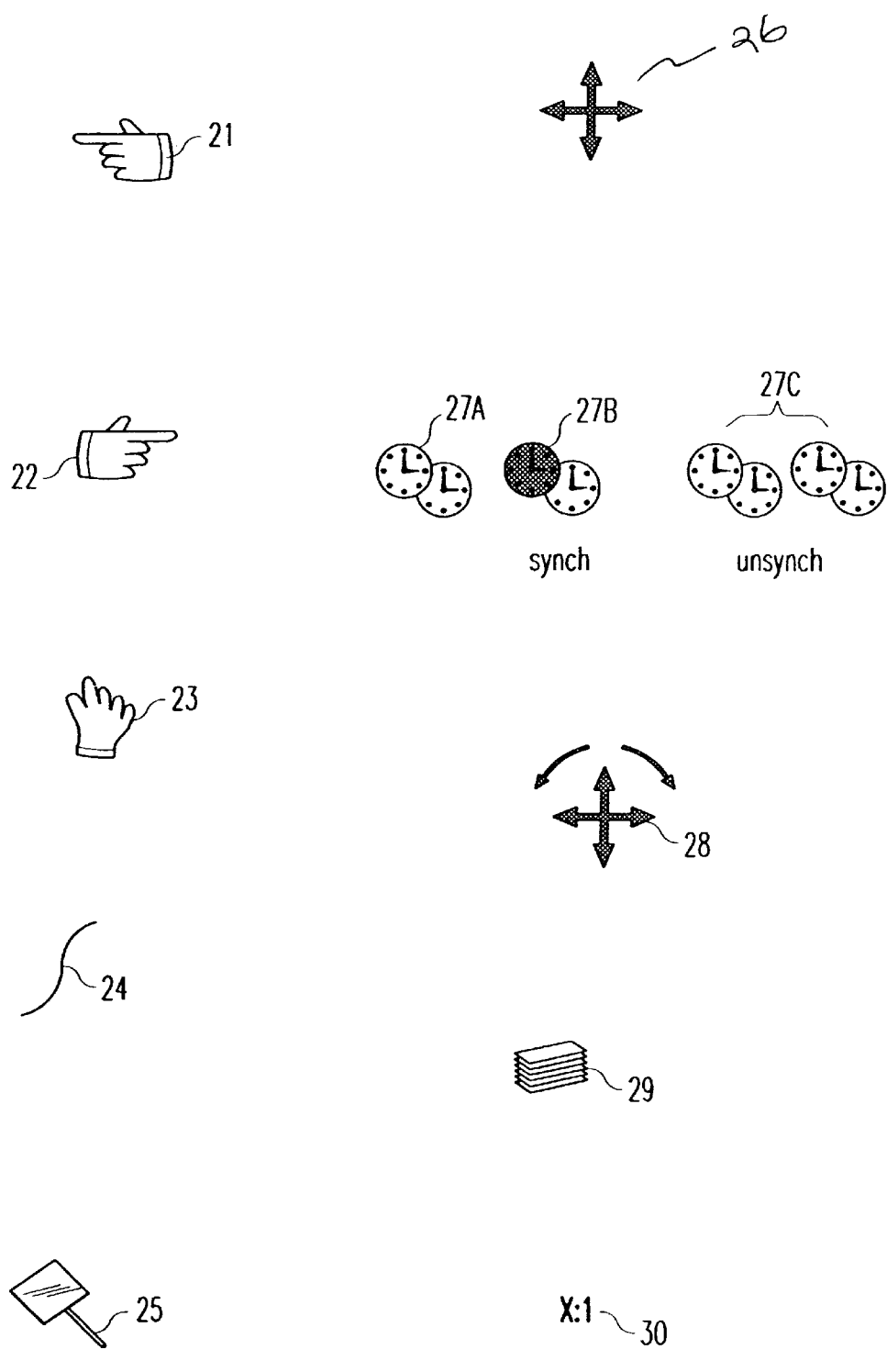
FIG. 12 illustrates the various cursor shapes according to a preferred embodiment of the present invention.

The left border region 101 is nominally a 20% border region on the left side of the active image display window 100 that allows the user to decrement or scroll backward through a group of images. When the cursor 20 lies within the left border region 101, its appearance is represented by a leftward pointing disarticulated hand 21 as shown in FIG. 12. In page display mode, a single click of the left mouse button 321 of FIG. 4 allows the user to move backward a page of images. In stack display mode, a single click of the left mouse button 321 allows the user to move one image backward through the stack of images.

Similarly, the right border region 102 is nominally a 20% border region on the right side of the active image display window 100 that allows the user to advance or scroll forward through a group of images. When the cursor 20 lies within the right border region 102, its appearance is nominally represented by a rightward pointing disarticulated hand 22 as shown in FIG. 12. In page display mode, a single click of the left mouse button 321 of FIG. 4 allows the user to move forward a page of images. In stack display mode, a single click of the left mouse button 321 allows the user to move one image backwards through the stack of images.

The bottom border region 103 is used for cinematic ("cine") speed control of the displayed images in the stack display mode. When the left mouse button 321 is depressed and not released, the images are played cinematically in an infinite forward loop or an infinite backward loop depending upon the position of the cursor 20. For example, when the cursor 20 lies on the right side of the stack, the cursor 20 takes on the appearance of a rightward pointing disarticulated hand 22 as shown in FIG. 12 and the images are played cinematically in an infinite forward loop. When the cursor 20 lies on the left side of the stack, the cursor 20 takes on the appearance of a leftward pointing disarticulated hand 21 as shown in FIG. 12 and the images are played cinematically in an infinite backward loop.

The cinematic speed control function can also be engaged by a single persistent click of the left mouse button 321. Once engaged, the cursor 20 is placed at the center of the bottom border region 103 of the active image display window 100. While engaged, the speed of the cinematic loop can be increased by sliding the cursor 20 to the right, or decreased by sliding the cursor 20 to the left.

The top border region 104 along the top of the active image window 100 allows the user to invoke a "grabbing hand" cursor 23, as shown in FIG. 12, to perform "drag and drop" image manipulation. The "grabbing hand" cursor 23 can be used to "drag and drop" individual images in the page display mode, or stacks of images in the stack display mode. Once the cursor 20 of FIG. 4 changes form, the user may engage it with a persistent click of the left mouse button 321, and virtually pick up and move the active image, or stack of images, unto another location on the image display monitor 10.

The "drag and drop" function associated with the top border-region 104 is further illustrated by the image display configuration shown in FIG. 2A. FIG. 2A shows a plurality of image display windows A through D in page display mode. The "drag and drop" function allows the image or stack of images in image display window A, for example, to be interchanged with the image or stack of images in image display window D. This feature is especially useful for grouping images or placing images side-by-side for comparison purposes.

Referring again to FIG. 4, an image, or stack of images, is "dropped" into place by releasing the left mouse button 321 when the image, or stack of images, is in the proximity of the desired drop point. A predefined "grid" enables the "dropped" image, or stack of images, to "snap" itself into alignment on the image display. This feature allows the user to rearrange images on the "canvas" of the monitor(s) much like film or slides on a conventional light box.

The window/level function region 105 allows the window and leveling adjustment of brightness and contrast. When the cursor 20 is in the window/level function region 105, the appearance of the cursor nominally changes to a sigma shape 24 as shown in FIG. 12. The window/level function may be engaged by a persistent click of the left mouse button 321 of FIG. 4, which allows the user to adjust the brightness and contrast to the user's preference. When the desired adjustment is achieved, release of the left mouse button 321 will fix the window/level to the desired setting. If the synchronization function is activated, as discussed below, all displayed images or stacks of images will be adjusted to the same window/level settings.

The magnification/zoom/panning function region 106 allows the user to perform magnification, zooming and panning functions on image of images in the active image display 100. The magnification function is activated by a persistent click of the left mouse button 321, whereupon the appearance of the cursor 20 nominally changes to a square magnifying glass 25, as shown in FIG. 12, while the left mouse button 321 remains depressed. The size of the square magnifying glass 25 can be varied by the user through administrative settings. In addition, the zoom function is activated by a double click of the left select button 321, and the panning function is activated by a persistent click of the right mouse button 323. The panning function is nominally indicated by the vertical and horizontal arrow cursor 26 as shown in FIG. 12. At a minimum, a single zoom must be performed before the panning function can be activated. A double click of the right mouse button 323 of FIG. 4 will un-zoom and un-pan the image to its original format.

The synch/unsynch function region 107 allows synchronized image manipulations on all images currently displayed, whether in page display mode or stack display mode. When the cursor 20 is in the synch/unsynch function region 107, the appearance of the cursor 20 nominally changes to a pair of small clocks 27A through 27C as shown in FIG. 12. The cursor 20 appears as a pair of identical white clocks 27A when the displayed images are in synchronized mode, and as a pair of clocks 27B, one white and one black, when the displayed images are in unsynchronized mode. When the in double synch mode, as described below, the cursor 20 appears as two pairs of identical white clocks 27C as shown in FIG. 12.

Referring again to FIG. 4, the synch/unsynch function behaves as a toggle state which is enabled and disabled by a single click of the left mouse button 321 while the cursor is within the synch/unsynch function region 107. When the synch state is enabled, all image manipulation functions, e.g., window/level, magnification/zoom/panning, etc., are applied to the images currently on display. When the unsynch state is enabled, subsequent image manipulation functions are applied only to those images in the active image window.

Also, when the synch state is enabled, the synch/unsynch function region 107 by default provides a double synch state by which all stacks are similarly manipulated by the window/level or magnification/zoom/panning functions. A single synch state may be engaged by a single click of the right mouse button 323 while the cursor 20 lies within the synch/unsynch function region 107. The single synch state allows the user to apply a series of manipulation functions, e.g., window/level, magnification/zoom/panning, etc., to an active stack of images in stack display mode, or to active images in page display mode, without applying the selected manipulation functions to each of all the other stacks or pages.

The rotation function region 108 allows the user to rotate the position of the displayed image or images In the active image display window 100. When the cursor 20 is in the rotation function region 108, the appearance of the cursor nominally changes to a montage of vectors 28 as shown in FIG. 12. The rotation function region 108 allows rotation of stacks, pages of images or individual images, depending upon the selected display mode and the synch state. The rotation function allows 90-degree rotation in a counterclockwise direction, 90-degree rotation in a clockwise direction, 180-degree rotation, and 180-degree mirror image rotation about the vertical axis of the image or stack of images.

Referring again to FIG. 4, the various manipulations associated with the rotation function region 108 are activated via single clicks of the left and right mouse buttons 321 and 323. A single click of the left mouse button 321 allows a 90-degree counterclockwise rotation of a stack, pages or individual image. Similarly, a single click of the right mouse button 323 allows a 90-degree clockwise rotation. In addition, a double click of the left mouse button 321 allows a 180-degree rotation, and a double click of the right mouse button 323 allows a 180-degree mirror image rotation about the vertical axis of image or stack images.

The stack/unstack function region 109 allows the user to stack or unstack a plurality of displayed images within the active image display window 100. When the cursor 20 is in the stack/unstack function region 109, the appearance of the cursor nominally changes to a stack of cards 29 as shown in FIG. 12. The stack/unstack function allows the user to operate the image display device in a page display mode, or "gestalt" mode, as shown in FIG. 2A, or a stack display mode as shown in FIG. 213, via a single click of the left mouse button 321 of FIG. 4.

Next, the image manipulation system as shown in FIG. 4 includes at least one display monitor 10. As illustratively shown in FIG. 2A, in page display mode the images displayed on a single monitor system are laid out in a sequence as if on a sheet of film. The images are displayed at a pre-determined "native" resolution fitting as many images in the image window 100 as permitted by the bitmap size of the image(s) and the resolution limits of the particular video card(s) and display monitor(s) being used. If the image bitmap exceeds the resolution of the video card(s) and display monitor(s), the image is sub-sampled and displayed in its entirety within the limits of the display monitor(s). In a single monitor configuration, the left and right border regions 101 and 102 are used to scroll forward and backward through the various images.

Figure 5:
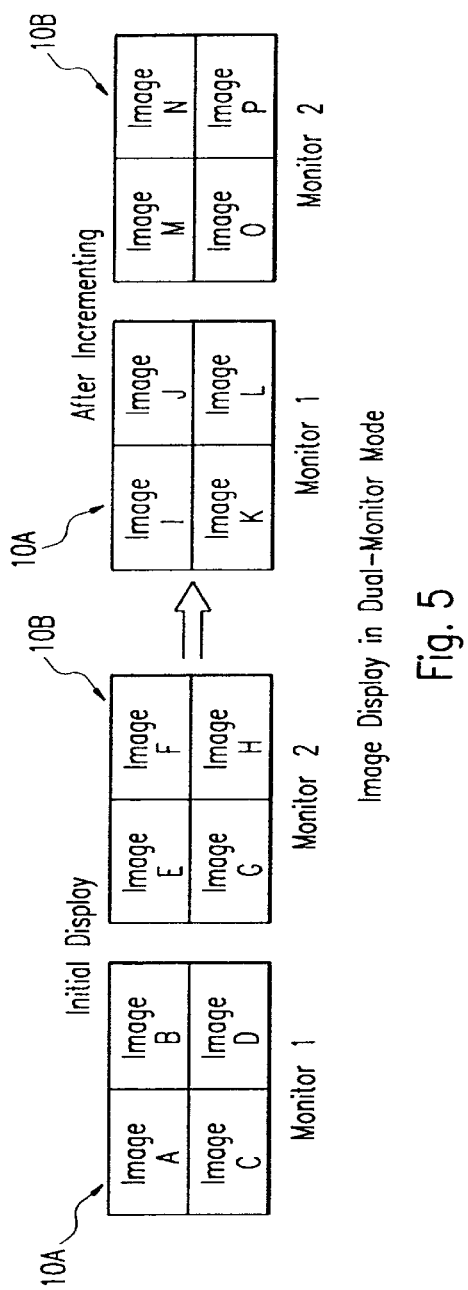
FIG. 5 is an illustration of an image display on a two-monitor, side-by-side display device according to a preferred embodiment of the present invention.

With multiple monitor configurations, as shown in FIG. 5, images not capable of being displayed on the first monitor 10A will be displayed from top left to right and in rows on a second monitor 10B. By placing the cursor 20 in the left or right 20% border regions of any image and clicking the left mouse button 321, the system will replace the images on both monitors starting with the next undisplayed image. For example, the initial display as shown in FIG. 5 is capable of showing only the first eight images A through H of the sixteen image set A through P. Accordingly, the right border region is used to increment the display to show the remaining images I through P.

Preferably, with single and multiple display monitors, groups of images or individual images associated with different studies are separated by a vertical gray line. Digital images may not always be displayed at their native resolution if the monitor(s) are too small. In addition, the digital images may be reduced or magnified both at the discretion of the user and/or by the limitations of the video card(s) and display monitor(s).

Figure 6B:
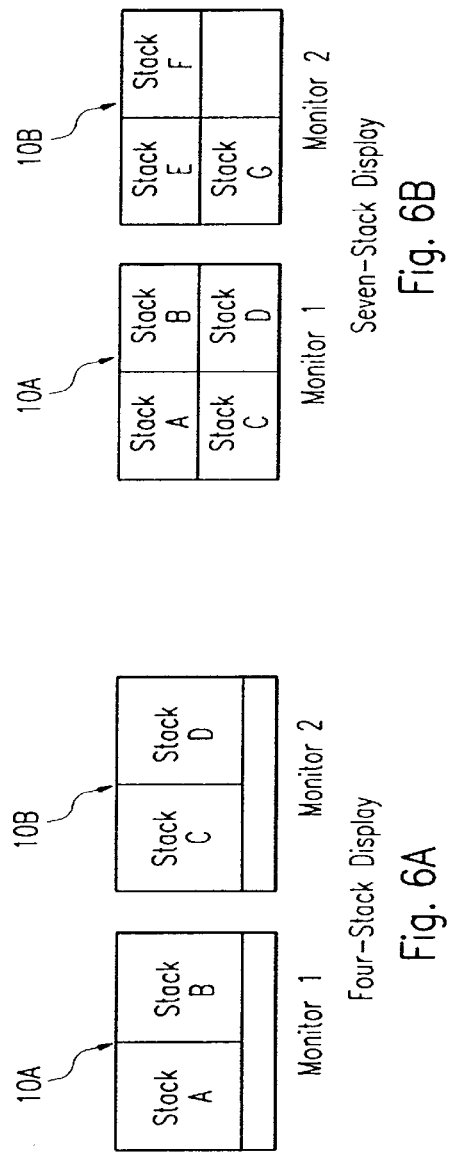
FIGS. 6A and 6B are illustrations of a four-stack image display and a seven-stack image display, respectively, on an two-monitor, stacked display device according to a preferred embodiment of the present invention.
Figure 6A:
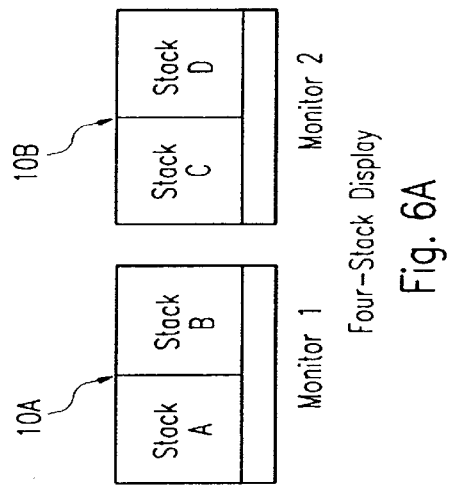

When viewing a plurality of stacks on multiple display monitors, stacks will be displayed in rows as illustratively shown in FIGS. 6A and 6B. FIG. 6A shows, for example, four stacks of images A through D displayed on a two-monitor device arranged in a side-by-side configuration. FIG. 6B shows seven stacks of images A through G displayed on a similar two-monitor device arranged in a side-by-side configuration. The stacks will be displayed in the order specified by the associated image data, e.g., the DICOM study and series information, but may be re-ordered at the discretion of the user by using the "drag and drop" function.

Referring again to FIG. 4, the image quantity function region 110 allows the user to decrease or increase the number of images displayed on a single monitor. When the cursor 20 is in the image quantity function region 110, the appearance of the cursor nominally changes to an "X:1" FIG. 30 as shown in FIG. 12. Preferably, the image quantity function allows the user to increment or decrement the number of displayed images by powers of two. For example, a single click of the left mouse button 321 decreases the number of displayed images by a power of two, whether in stack display or page display mode. Likewise, a single click of the right mouse button 321 of FIG. 4 increases the number of displayed images by a power of two.

The active image display window 100 can optionally be partitioned into a plurality of variably sized virtual spaces. With this feature, the sizes of virtual spaces 101 through 110, as shown in FIGS. 1 and 4, for example, can be determined by the amount of usage afforded to each of the virtual spaces 101 through 110. The more often a particular function is used, the larger the amount of space that function is given on the display.

The geographic locations of the virtual spaces 101 through 110 of FIGS. 1 and 4, as well as the image manipulation functions mapped thereto, can also be assigned and modified as desired by the user. In addition, the geographic locations and functions can be assigned and modified by the user depending upon the type of image or images being displayed, e.g., X-ray, magnetic resonance ("MRI"), computer tomography ("CAT"), nuclear medicine ("NM"), ultrasound ("U/S") images, etc. For example, the user may wish to use different spaces or different image manipulation functions for plain X-rays as compared to CAT scan images, taking advantage of their unique characteristics, and similarly the user may wish to map different spaces and image manipulation functions for U/S images as compared to MRI images.

In addition, the image manipulation system of FIG. 4 also includes a disappearing/reappearing pop-up toolbar 11 as shown in FIGS. 11A through 11D. Although shown as appearing along the top of the image display areas of display monitors 10A through 10D, the pop-up toolbar 11 can be made to disappear or reappear at any location on the image display areas, preferably by striking the middle mouse button 322 of FIG. 4. The actual location of the pop-up toolbar 11 coincides with the position of the cursor 20 when the middle mouse button 322 is depressed. The pop-up toolbar contains bitmapped pushbuttons which allow the activation of various tools and actions including but not limited to window/level, magnification/zoom/pan, synch/unsynch, white/black inversion, next case/study, prior case/study, rotate, etc.

Figure 11A:
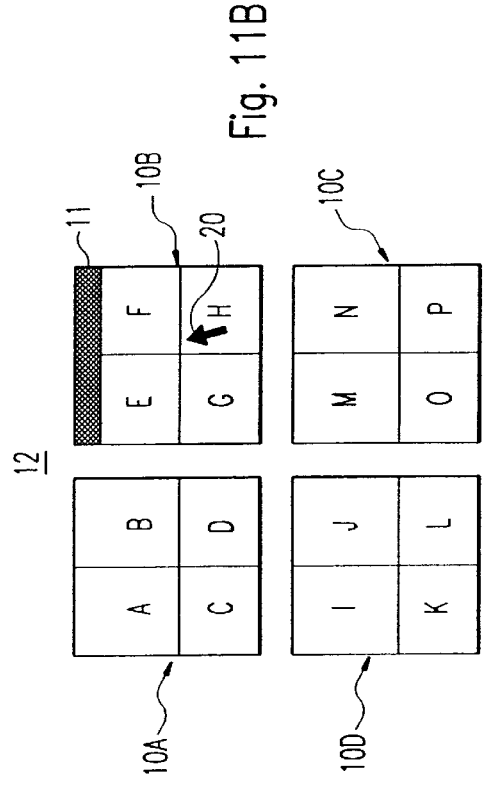
FIGS. 11A through 11D are illustrations of an image display on a four-monitor, stacked display device with a "disappearing/reappearing" pop-up toolbar according to a preferred embodiment of the present invention.
Figure 11B:
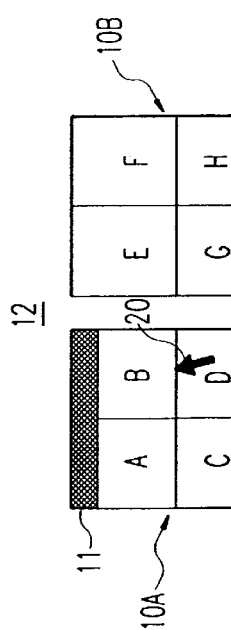
Figure 11C:
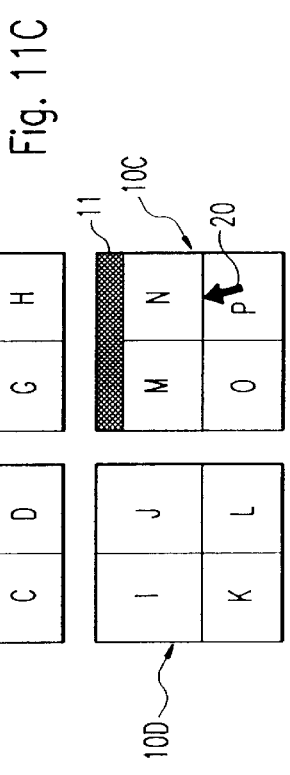
Figure 11D:
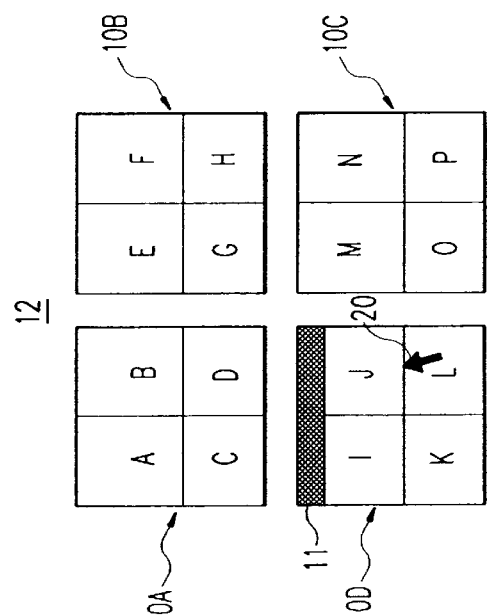

The pop-up toolbar 11 of FIGS. 11A through 11D is also characterized by a "follow-around" feature whereby the pop-up toolbar 11 "follows" the cursor as it moves from display monitor to display monitor in a multiple display monitor configuration. FIGS. 11A through 11D, for example, show a four-monitor, stacked display device 12 with image windows A through P. The display device 12 includes display monitors 10A through 10D, pop-up toolbar 11, cursor 20 and preferably a mouse (not shown) for controlling the cursor 20. As shown by the sequence of FIGS. 11A though 11D, the pop-up toolbar 11 "follows" the cursor 20 as it is moved from display monitor 10A to display monitor 10B, from display monitor 10B to display monitor 10C, and then from display monitor 10C to display monitor 10D.

The "disappearing/reappearing" and "follow-around" characteristics of the pop-up toolbar 11 are especially advantageous in radiology and medical imaging applications in that the pop-up toolbar 11 is mainly non-intrusive thereby allowing maximum use of the image display areas. In addition, use of the pop-up toolbar 11 is advantageous in that ambient light emitted from the image display area/user interface is reduced and "bum-in" of pushbuttons on high luminescence monitors is eliminated.

Figure 13:
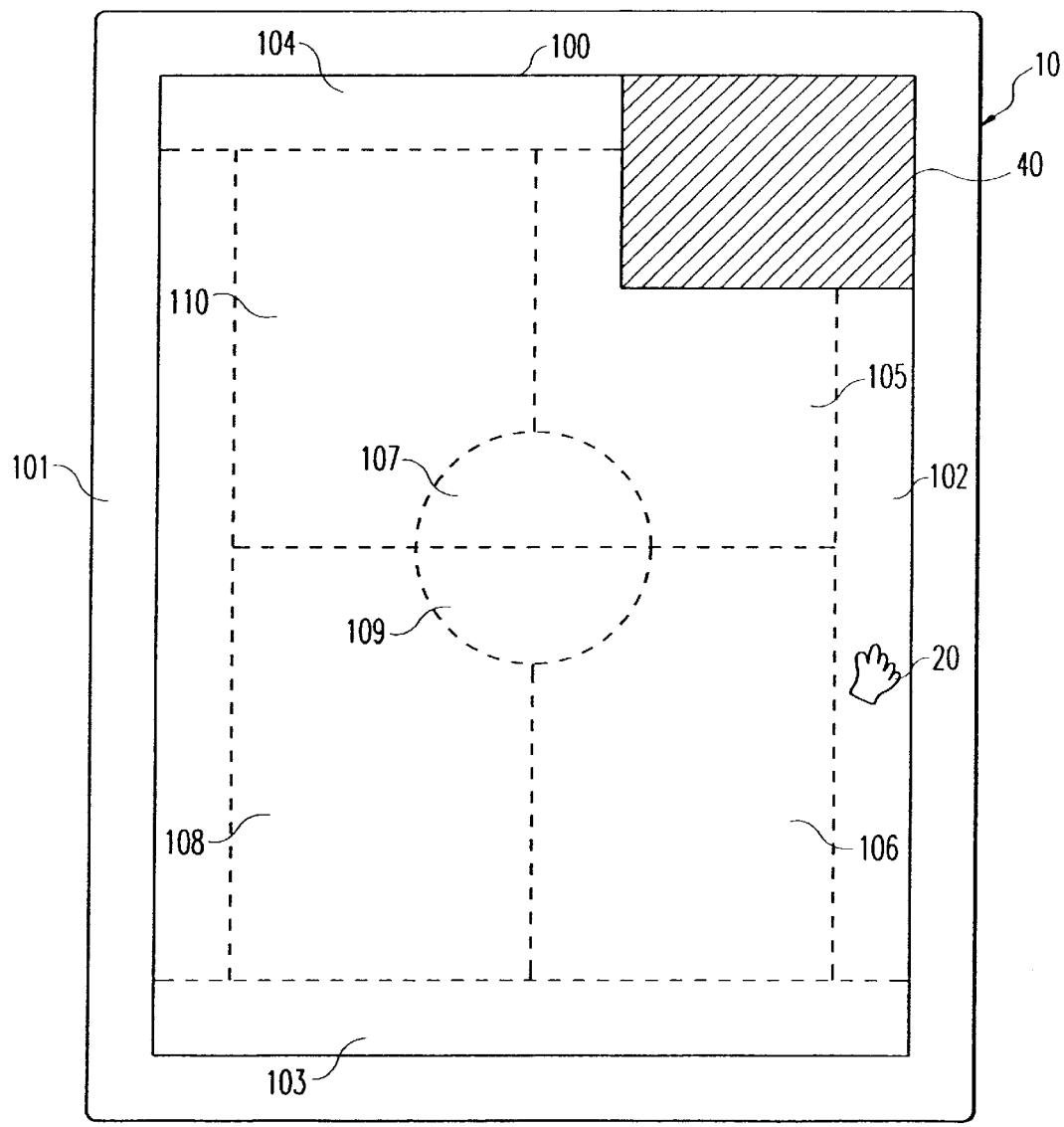
FIG. 13 is an illustration of a "sticky" virtual area according to the preferred embodiment of the present invention.

In addition, the image manipulation system of FIG. 4 also includes a "sticky" virtual area 40 as shown in FIG. 13. "Sticky" virtual area 40, shown in FIG. 13 by way of example and not limitation, is used for temporarily "hanging" or storing digital images while they are re-arranged on the image display.

Other features of the image manipulation system of FIG. 4 may include a plurality of pop-up menus (not shown) for providing the same functionalities available through the pop-up toolbar 11. Preferably, the pop-up menus are invoked by single clicks of the right mouse button 323. A speed control panel (not shown) is also provided for controlling image viewing speeds in cine mode.

Figure 7:
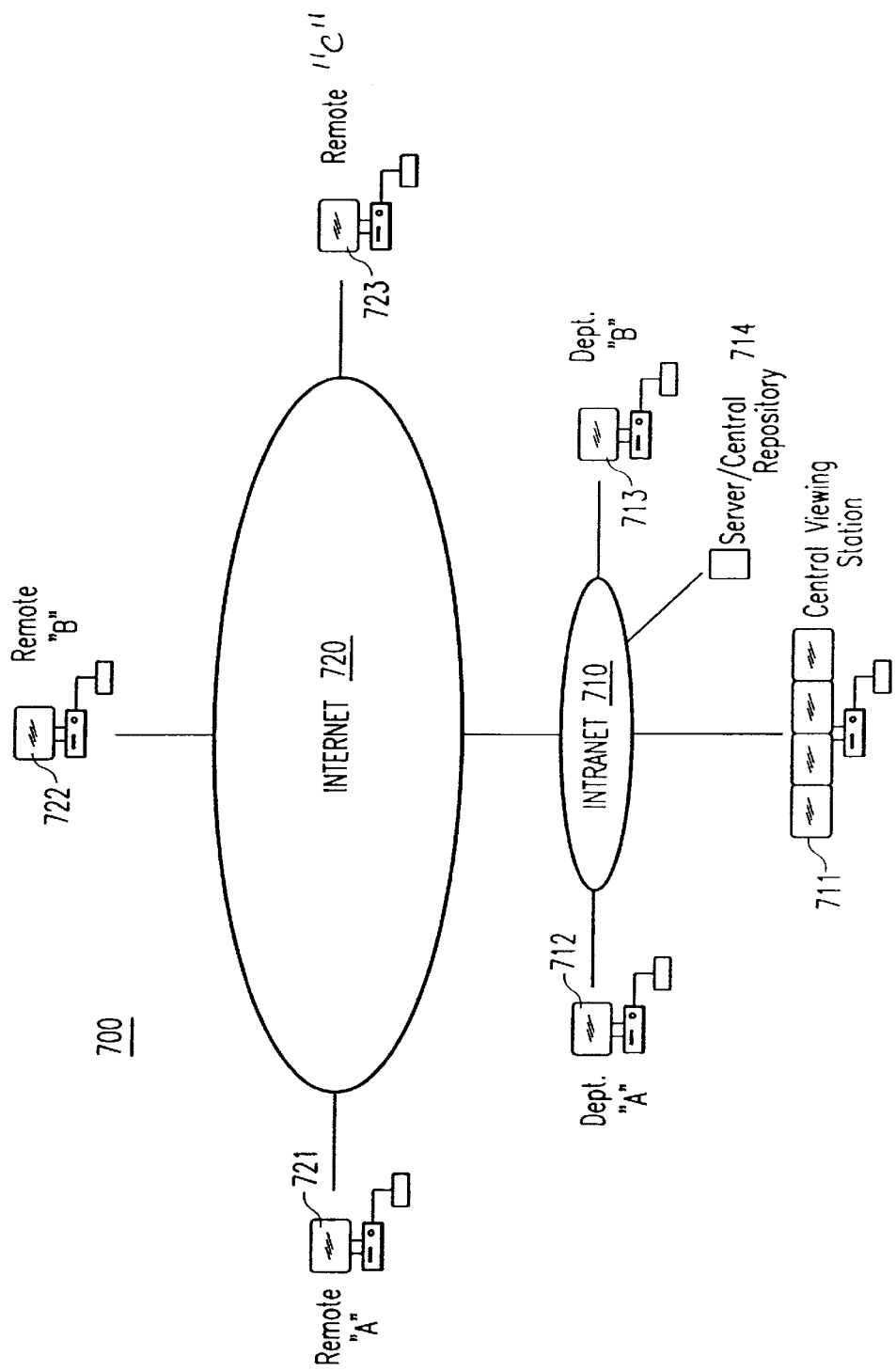
FIG. 7 is a schematic of an image manipulation system adapted for use in local area and wide area networks according to a preferred embodiment of the present invention.

FIG. 7 shows another preferred embodiment of the present invention, wherein an image manipulation system 700 is provided for use with Local Area Networks ("LAN's") 720, i.e., intranet networks, and Wide Area Networks ("WAN's") 710, where a WAN 710 can utilize the Internet for example. As shown in FIG. 7, the image manipulation system 700 includes: a central repository or server 714 for providing image data corresponding to digital images; a central station 711 for processing the image data and for viewing and manipulating the digital images; a first network 710 connected to the central repository 714, the first network 710 having at least one local site, and least one local node 711 through 713 at the local site for processing the image data and for viewing and manipulating the digital images; and a second network 720 a connected to the central repository 714 having at least one remote site, and at least one remote node 721 through 723 at the remote site for processing the image data and for viewing and manipulating the digital images.

Figure 8:
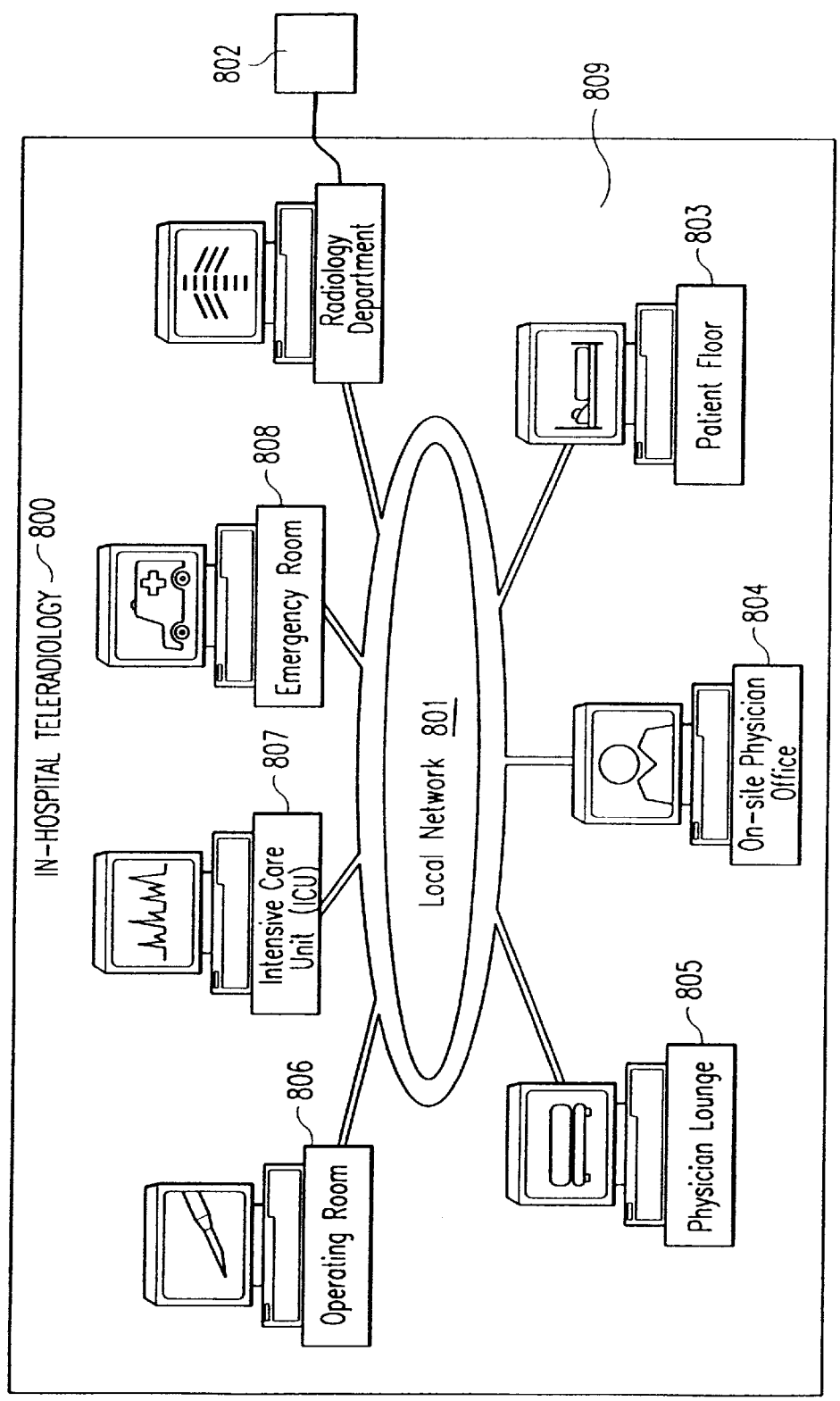
FIG. 8 is a schematic of an image manipulation system adapted for in-hospital teleradiology.

FIG. 8 shows another preferred embodiment of the present invention wherein an image manipulation system is provided for in-hospital teleradiology. As shown in FIG. 8, the image manipulation system for in-hospital teleradiology 800 includes: a central repository 802 for providing image data corresponding to digital images; a central station 809 for processing the image data and for viewing and manipulating the digital images; and a local network 801 connected to the central repository 802, the local network 801 including at least one local site connected to the central repository 802, and at least one local node 803 through 808 at the local sites for processing the image data and for viewing and manipulating the digital images. For example, the local sites may include one or more of the operating rooms, intensive care unit, emergency room, patient floors, on-site physician offices and physician lounge. Preferably, the image manipulation system for multi-site teleradiology is DICOM-compatible. The central repository can then include or be connected to any radiology, laboratory or research information system that is DICOM compatible.

Figure 9:
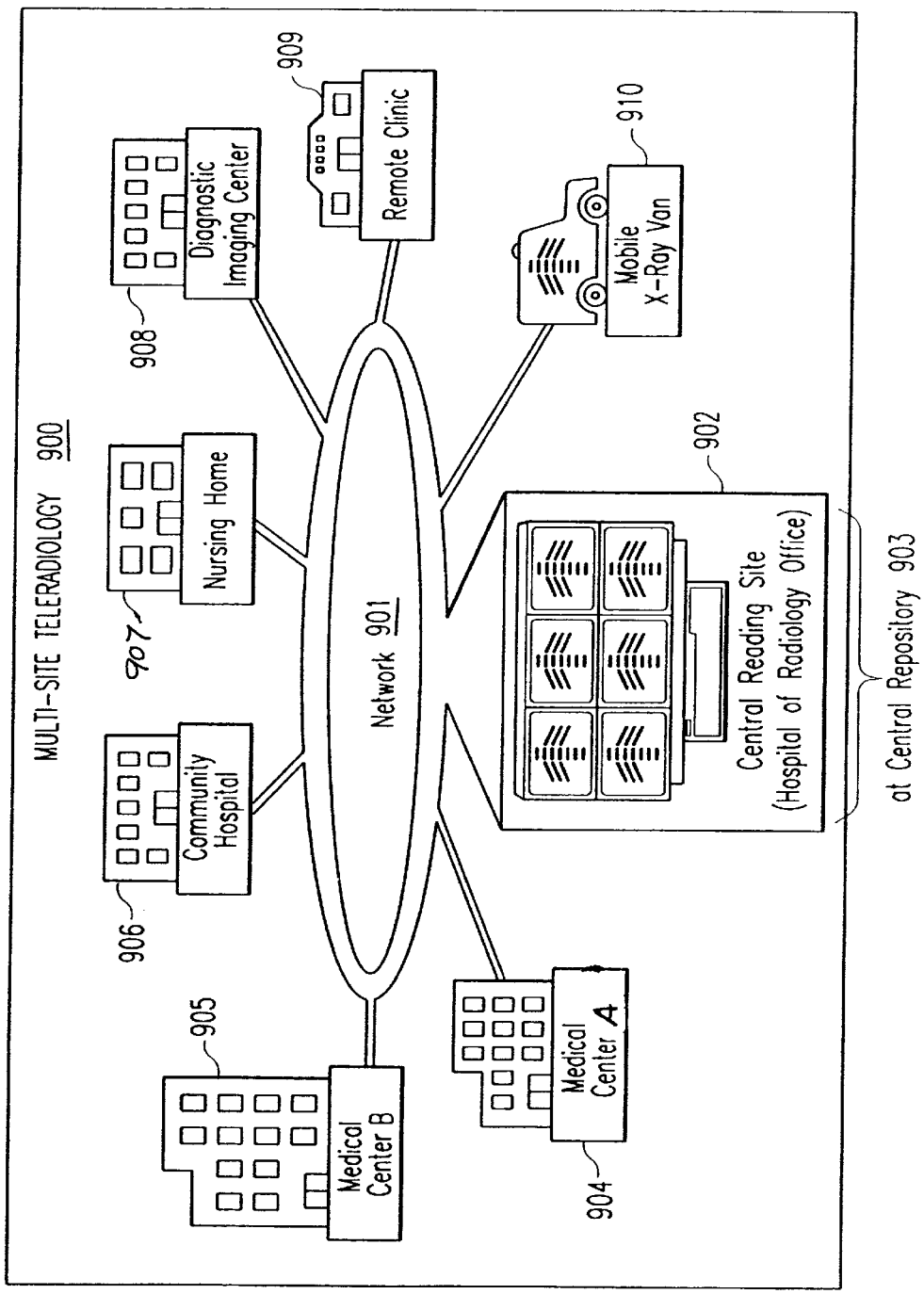
FIG. 9 is a schematic of an image manipulation system adapted for multi-site teleradiology.

Another preferred embodiment of the present invention is an image manipulation system 900 provided for multi-site teleradiology as illustrated in FIG. 9. The system for multisite teleradiology 900 includes: a central repository 903 for providing image data corresponding to the digital images; a central station 902 for processing the image data and for viewing and manipulating the corresponding digital images;

and a network 901 connected to the central repository 903. The network has one or more remote sites each with one or more remote nodes 904 through 910 at the remote site for processing the image data and for viewing and manipulating the digital images. Again, the image manipulation system for multi-site teleradiology is preferably DICOM-compatible.

The remote sites of the nodes 904 through 910 correspond to remote sites commonly associated with hospital and health care information systems. These remote site nodes, for example, may include, but are not limited to, medical center nodes 904 and 905, a community hospital node 906, a nursing home node 907, a diagnostic imaging center node 908, a remote clinic node 909 and a mobile X-ray van node 910. The central repository can include or be connected to any radiology, laboratory or research information system that is DICOM compatible.

The image manipulation systems of FIGS. 7 through 9 include image display windows that are partitioned geographically into virtual spaces when activated. As shown in FIGS. 1 and 4, the virtual spaces are in turn mapped to instructions or tools for performing image manipulation functions on the image or images displayed in the activated image display window. X-ray, MRI, CAT, NM and U/S images, for example, can be displayed in stack or page display modes, and unique multi-function image display pushbuttons are provided for fast image manipulation. Other functionalities of the present invention as shown in FIGS. 7 through 9 and described above in connection with FIG. 4 include: magnify/zoom/pan, rotate and flip, window and leveling, multi-image display, floating image toolbar, image annotation, cinematic mode image display, and image "sticky" display areas.

In addition, the image manipulation systems of FIGS. 8 and 9 can be high performance, 32-bit applications adaptable for use over conventional dial-up phone lines or Integrated Services Digital Network ("ISDN") lines. Also, the systems of FIGS. 8 and 9 can be adapted for use with WAN and LAN networks using Ethernet, frame relay, Fiber Distributed Data Interface ("FDDI"), Asynchronous Transfer Mode ("ATM"), T-1 line and satellite link technologies. Preferably, a DICOM-compatible embodiment of the present invention provides full 12-bit window and level for native DICOM images, and gradient density control for plain films. Also, when viewing a plurality of digital images, digital images can be reviewed while receiving data for the remaining digital images.

In accordance with the present invention, a method is disclosed for manipulating digital images. The method includes the steps of displaying at least one of a plurality of digital images on at least one of a plurality of display monitor members, each of the display monitors including at least one of a plurality of image display windows, wherein each of the image display windows is capable of displaying at least one of the digital images; designating virtual spaces of each of the image display windows as function executing, the designating means including a cursor and instructions associated with the virtual spaces; generating the instructions associated with the virtual spaces; assigning each of the virtual spaces with image manipulation functions corresponding to a position of the cursor when located within each of the virtual spaces; and executing the instructions associated with each of the virtual spaces.

Figure 10:
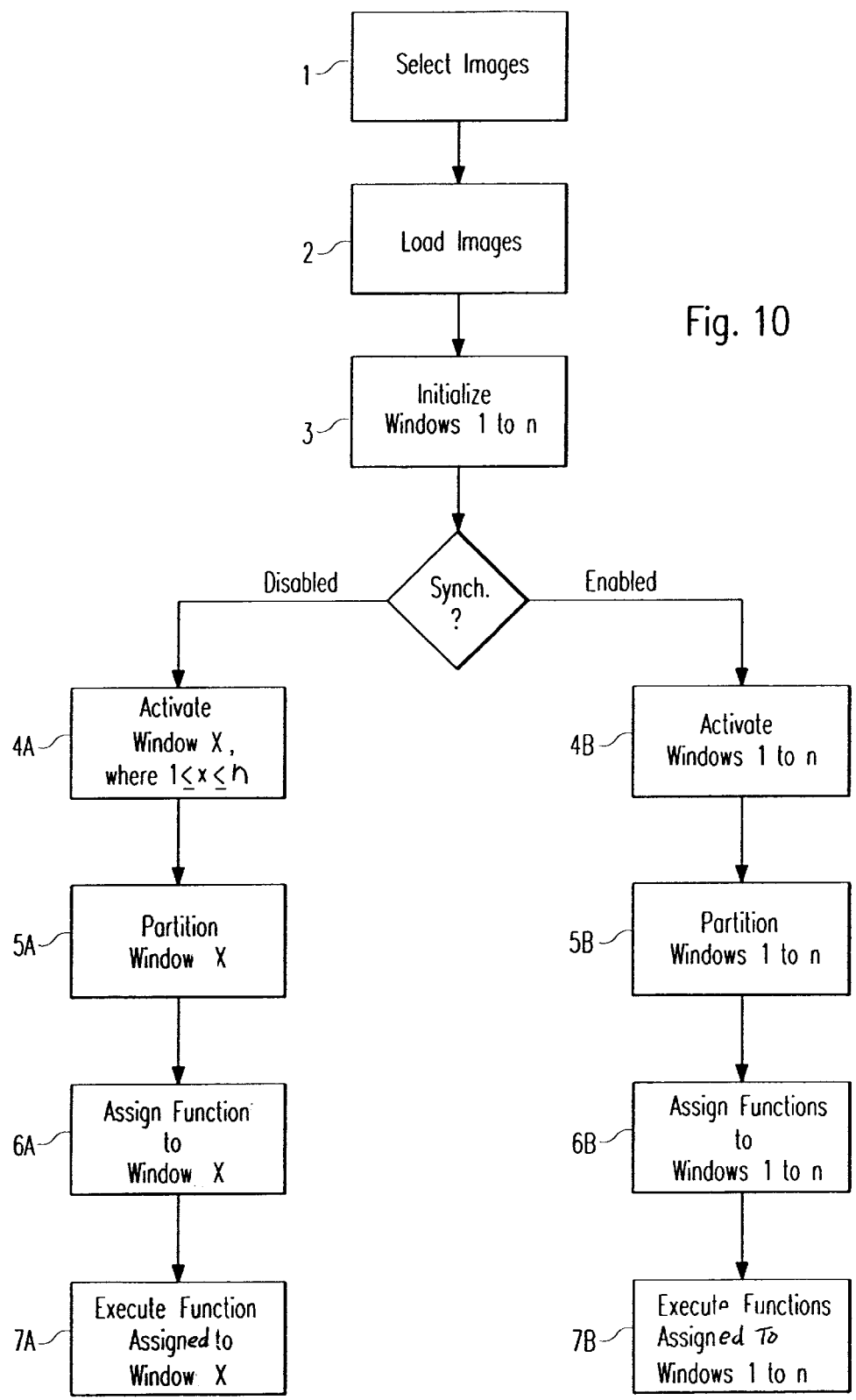
FIG. 10 is a flow chart of a method for directly manipulating digital images.

In accordance with the present invention, another method is disclosed for manipulating digital images. As shown in FIG. 10, the method of the present invention includes the steps of selecting at least one of a plurality of digital images to be displayed (Step 1); loading image data associated with the digital images into computer memory (Step 2); initializing at least one of a plurality of image display windows I to n for displaying the digital images (Step 3); activating one of the image display windows X (Step 4A); partitioning the activated image display window X into a plurality of regions (Step 5A); assigning each of the regions to a set of instructions required for performing one of a plurality of image manipulation functions associated with each of the regions within the activated image window X (Step 6A); executing a selected one of the image manipulation functions within the activated image display window X (Step 7A), the executing step (Step 7A) including the steps of moving a cursor into the region associated with the selected image manipulation function, and manually engaging instructions associated with the selected image manipulation function. This method is operative when a synch flag is disabled. In addition, when the synch flag is enabled, the step of executing the image manipulation functions can be synchronized to effect a plurality of image display windows I to n simultaneously (Steps 1–3, 413–7B).

In accordance with yet another aspect of the present invention, a computer program is provided for use with a system for directly manipulating digital images with a pointing device. The computer program includes a computer usable medium and a computer readable program code embodied therein for: displaying at least one of a plurality of digital images on at least one display monitor, the display monitor comprising at least one of a plurality of image display windows, wherein each of the image display windows is capable of displaying at least one of the digital images; designating virtual spaces of each of the image display windows as function activating by way of a cursor and instructions associated with the virtual spaces; generating the instructions associated with the virtual spaces; assigning each of the virtual spaces with a unique function corresponding to a position of the cursor when located within each of the virtual spaces; and for executing the instructions associated with each of the virtual spaces.

Figure 14:
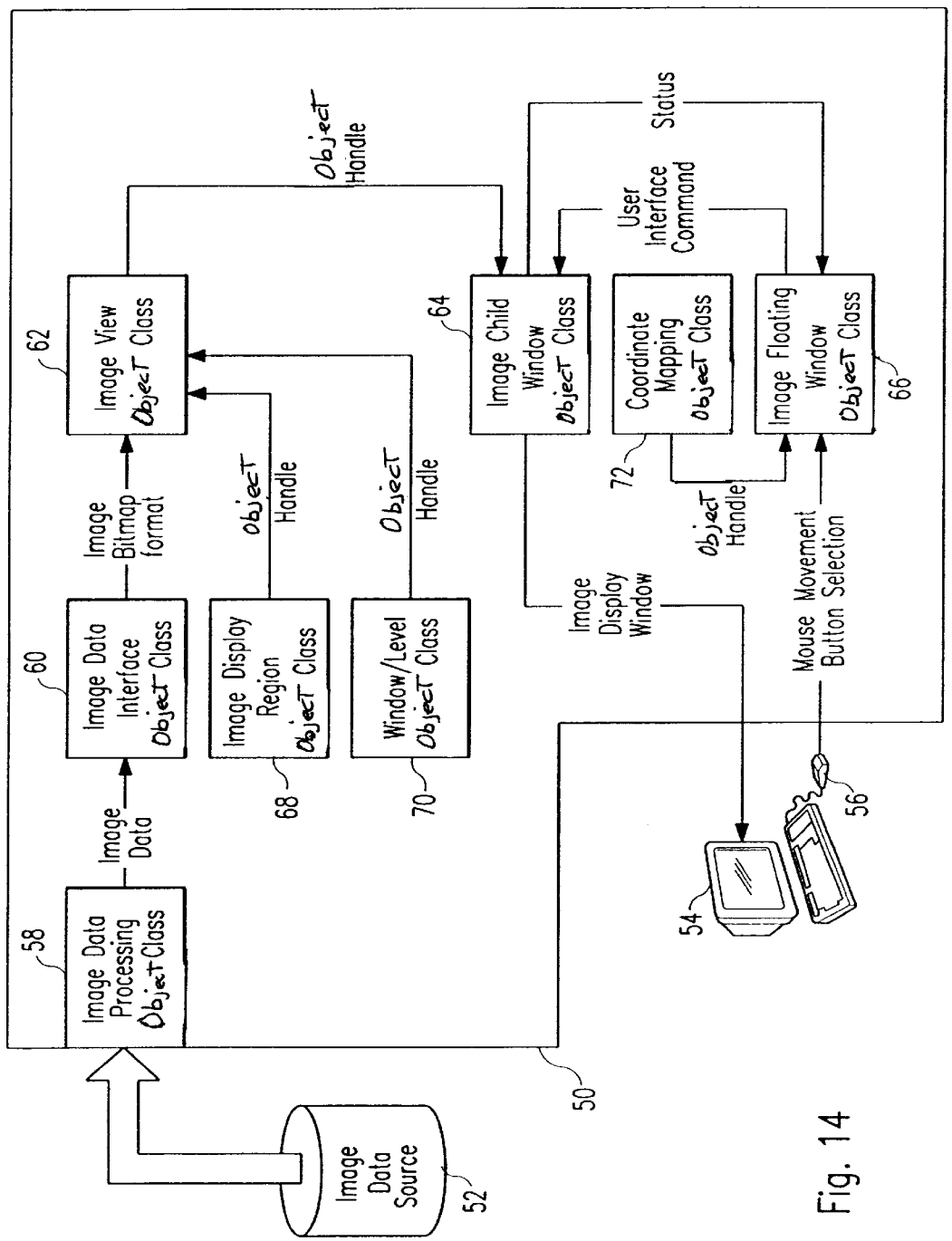
FIG. 14 is a data flow diagram of a computer program for image manipulation according to a preferred embodiment of the present invention.

FIG. 14 shows a data flow diagram of a computer program 50 for use with an image manipulation system according to a preferred embodiment of the present invention. The data flow diagram describes the flow of information from an image source 52 to the displayed image or images on one or more display monitors 54. The rectangles 58 through 72 represent the object classes used by the computer program to perform various image manipulation functions. The lines between the object classes 58 through 72 represent the information being passed from one object class to another.

As further shown in FIG. 14, the computer program for use with an image manipulation system includes a computer usable medium and a computer readable program code 50 embodied therein. The computer readable program code further includes: an image data processing object class 58; an image data interface object class 60; an image view object class 62; an image floating window object class 66; an image child window object class 64; an image display region object class 68; a window/level object class 70; and a coordinate mapping object class 72.

The image data processing ("Image1") object class 58 is a "low-level" object class that provides a plurality of common image data processing services. "Low-level" in this context refers to accessibility by "low-level" or "function level" applications programmers, as opposed to access by "high-level" users. The Image1 object class 58 provides such functions as loading, writing and saving of image data.

The image data interface ("ImageIntrf") object class 60 is a "high-level" object class that provides an interface between the image data and the computer readable program code. For example, in DICOM-compatible systems, the ImageIntrf object class 60 provides an interface to a DICOM files containing image data. The ImageIntrf object class 60 receives the DICOM files, and must first decipher the DICOM image header data associated with the file. The DICOM image header may contain, for example, a patient identification field, a patient name field, a study instance user identification field, a study date field, a study time field, a series instance user identification field, an image instance service object pair ("SOP") and image number field.

The ImageIntrf object class 60 then creates one or more ImageIntrf objects containing image bitmap data corresponding to each of the images to be displayed. If any of the required fields are missing, the ImageIntrf object class 60 in a DICOM-compatible system will reject the image data, forward a message to an events log, and store the rejected file in a default or designated subdirectory at a local processor.

The ImageIntrf objects created by the ImageIntrf object class 60 may include image data of various formats, e.g., device independent bitmap ("DIB" or "raw pixels"), DICOM file format, etc. Image data provided by the ImageIntrf object class 60 may also include autowindow/level, miniature token-style DIB depicting the image, and change notifications for windows. The ImageIntrf object class 60 may also perform geometric manipulations such as rotation, flipping, zoom factor, position of image, gray scale inversion and window/level setting.

The image view ("ImageView") object class 62 processes the image bitmap data and for displaying one or more images in one or more display areas on one or more display monitors 54. The ImageView object class 62 is a "pseudo-low-level" object class that displays an object corresponding to the image child window ("ImageChildWin") object class 64 in an area defined by the image floating window ("ImageFloatingWin") object class 66 and the image display region ("ImageDispRegion") object class 68. The Imageview object class 62 has an object handle, or pointer, to the ImageChildWin object class 64, and is primarily responsible for displaying an image or group of images in a window, region of a window, or other type of display areas. The Imageview object class 62 also superimposes window, level and grayscale inversion settings on the displayed image.

In a Windows-compatible system, the Imageview object class 62 supports window handles ("HWND's") and device context handles ("HDC's"). An HWND is a handle which is returned by the operating system when a window is created. Likewise, an HDC is obtained by the application to obtain various information such as palette information, coordinate mapping mode and pixel mapping mode. In addition, it can also provide a means for displaying the image information.

The ImageView object class 62 is a "pseudo-low-level" object class partly because it does not own an image window or provide the image window's window procedure. Instead, the ImageView objects perform tasks, e.g., image draw/redraw, magnifier creation/destruction, window/level change, pan/zoom, changing which image is displayed, etc., only when the applications programmer calls the appropriate member functions of the ImageChildWin object class 64. This permits superior customization by applications programmer. ImageView object class 62 functions for converting between inageDispRegion object class 68 and ImageIntrf object class 60 coordinate systems support layering by applications programmer of items such as DICOM text overlays, which provide template information for DICOM images.

The ImageChildWin object class 64 is used for mapping the image interface objects to one or more image display windows within the display areas. ImageChildWin objects are created and configured indirectly through the ImageFloatingWin object class 66. Each ImageChildWin object represents a child window that displays one ImageIntrf object, and provides user interface capabilities for performing various image manipulation functions such as pan/zoom, set window/level, etc. User-programmer may configure some behaviors such as parameters, the ImageIntrf objects settings, replace the ImageIntrf objects, different window/level settings, etc. Each ImageChildWin object is also capable of providing status of the image information such as the geometric orientation, window/level setting, zoom level and gray scale inversion status.

The ImageFloatingWin object class 66 is used for defining the display areas on one or more display monitors 54, and further includes a user interface for executing image manipulation functions. Each of ImageFloatingWin objects represent a floating window (not child window) that displays one or more ImageIntrf objects on one or more display monitors 54. Each ImageFloatingWin object also provides user interface capabilities for performing various image manipulation functions such as pan/zoom, set window/level, etc. The user-programmer may also configure some behaviors as parameters, set the ImageIntrf objects, replace the ImageIntrf objects, create with specified window/level settings, etc. This class utilizes ImageChildWin objects to create the ImageIntrf objects and is ultimately responsible for displaying one or more image display windows on the display monitors.

The remaining classes, the ("ImageDispRegion"), window/level ("WLSetting") and coordinate mapping ("DrawMapping") object classes 68, 70 and 72 respectively, include parameters that are passed to the member functions of the other object classes 58, 60 62, 64 and 66. For example, a WLSetting object belonging to the WLSetting object class 70 may be passed to an ImageView object to set the Window/Level setting of 12-bit images being displayed.

The ImageDispRegion object class 68 corresponds to a region which may be used for image display. Supported types of ImageDispRegion objects include window, window region, and HDC, e.g., a HDC for a printer page being printed. The ImageDispRegion object class 68 has an object handle to the ImageView object class 62, and provides region dimensions data, HWND and/or HDC, if available, to the ImageView object class 62. This is sometimes used as a parameter to image display object service functions.

The WLSetting object class 70 represents a window (window width), level (window center), and grayscale inversion setting, including the significant bits per pixel and the maximum and minimum values for each pixel. The WLSetting object class 70 has an object handle to the to the ImageView object class 62, and is useful for storing window/level/invert settings, passing them between objects and into and out of modules, and for converting between different ways of representing window and level. The WLSetting object class 70 also converts between different numbers of significant bits, so, for example, users viewing 10-significant-bit-per-pixel images may use familiar 12-significant-bits-per-pixel scales for window and level.

In DICOM applications, the WLSetting object class 70 is especially useful because the number of window/level significant bits used by different communities vanes according to different standards. The WLSetting object class 70 is also useful where presets for 12-bit images may need to be applied rationally to 10-bit images or 13-bit images.

The DrawMapping object class 72 defines a mapping between two coordinate spaces, such as between an image coordinate space and an image window coordinate space in which the image is displayed. This is sometimes used as a parameter that is passed to image display object service functions. The DrawMapping object class 72 has an object handle to the ImageFloatingWin object class 66.

Figure 15:
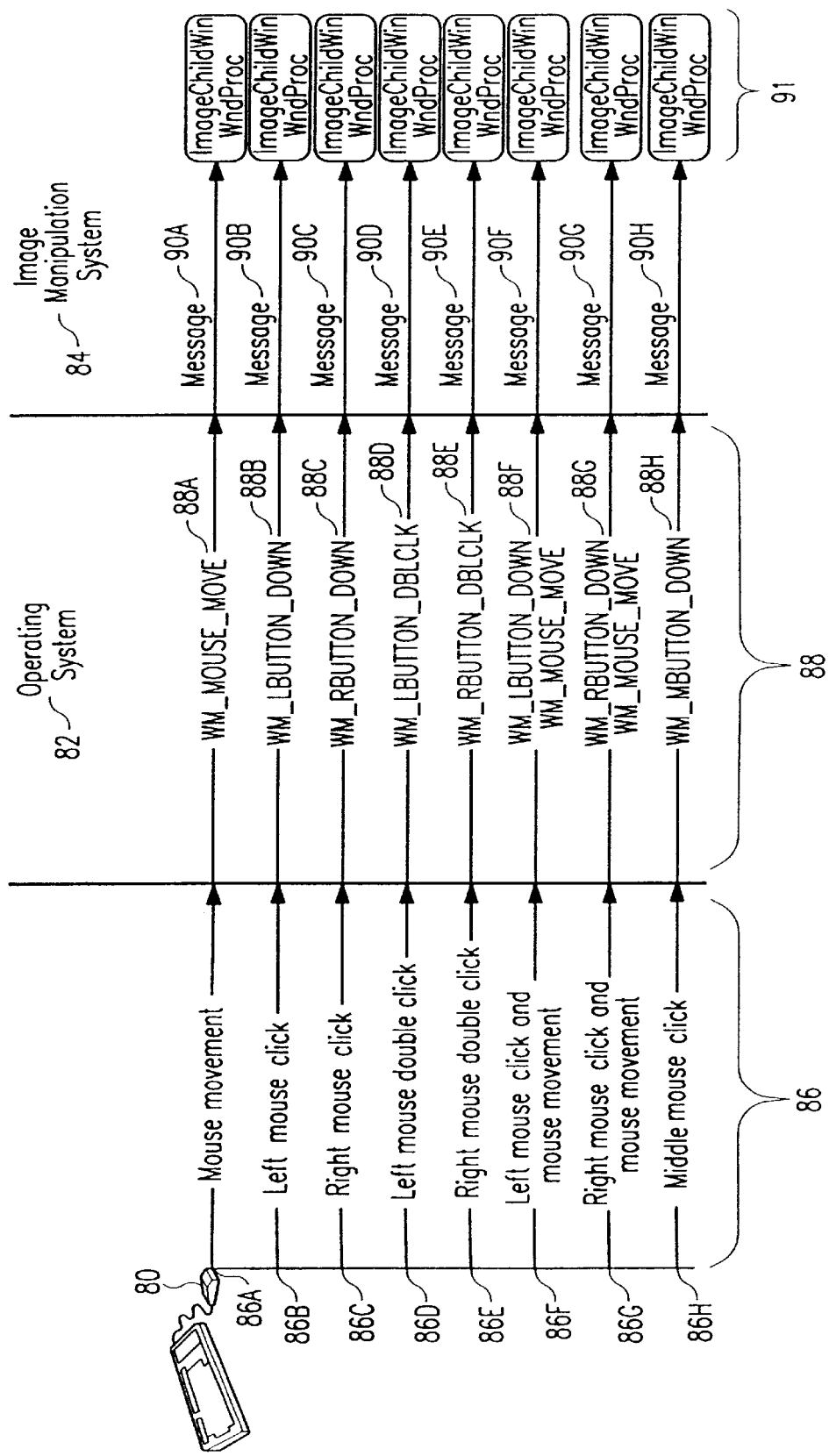
FIG. 15 is a events diagram for the computer program of FIG. 14 according to a preferred embodiment of the present invention.

FIG. 15 is a events diagram associated with the computer program of FIG. 14. As shown in FIG. 15, the image manipulation system and computer program utilize an event-driven mechanism to efficiently capture user commands, i.e., mouse clicks, and mouse movements generated by the user with mouse 80. These user commands and mouse movements 86 (also shown as 86A through 86H) correspond to the various image manipulations performed by the user via the mouse 80 as the primary input device. User commands and mouse movements 86 include but are not limited to mouse movement 86A, a left mouse button click 86B, a right mouse button click 86C; a left mouse button double click 86D; a right mouse button double click 86E; a left mouse button click combined with mouse movement 86F; right mouse button click combined with mouse movement 86G; and middle mouse button click 86H.

As further shown in FIG. 15, the user commands and mouse movements 86 trigger the various events 88 (also shown as 88A through 88H) in the operating system kernel 82. The events 88 correspond to the user commands and mouse movements 86A through 86H and include: WM_MOUSE_MOVE 88A, which occurs when a mouse movement 86A is detected; WM_LBUTTON_DOWN 88B, which occurs when a left mouse button click 86B is detected; WM_RBUTTON_DOWN 88C, which occurs when a right mouse button click 86C is detected; WM_LBUTTON_DBLCLK 88D, which occurs when a left mouse button double click 86D is detected; WM_RBUTTON_DBLCLK 88E, which occurs when a right mouse button" double click 86E is detected; WM_LBUTTON_DOWN-WM_MOUSE_MOVE 88F, which occurs when a left mouse button click combined with a mouse movement 86F is detected; WM_RBUTTON_DOWN-WM_MOUSE_MOVE 88G, which occurs when a right mouse button click combined with a mouse movement 86G is detected; and WM_MBUTTON_DOWN 88H, which occurs when a middle mouse button click 86H is detected.

Each of the aforementioned events 88A through 88H in turn generates corresponding messages 90A through 90H, which are then passed to the image manipulation system 84. As shown in FIG. 14, the message 90A through 90H are further passed as user interface commands from the ImageFloatingWin object class 66 to the ImageChildWin objects 10, associated with each of the image display windows being utilized. Referring again to FIG. 15, the messages 90A through 90H coming from the operating system kernel 82 are ultimately processed by the WndProc event handler function 91, which is one of the member functions in the ImageChildWin objects. In the ImageChildWin object class, the WndProc event handler function 91 maps the user interface command to a region or virtual space on the image display window to determine what image manipulation function is performed on the displayed image.

Figure 16:
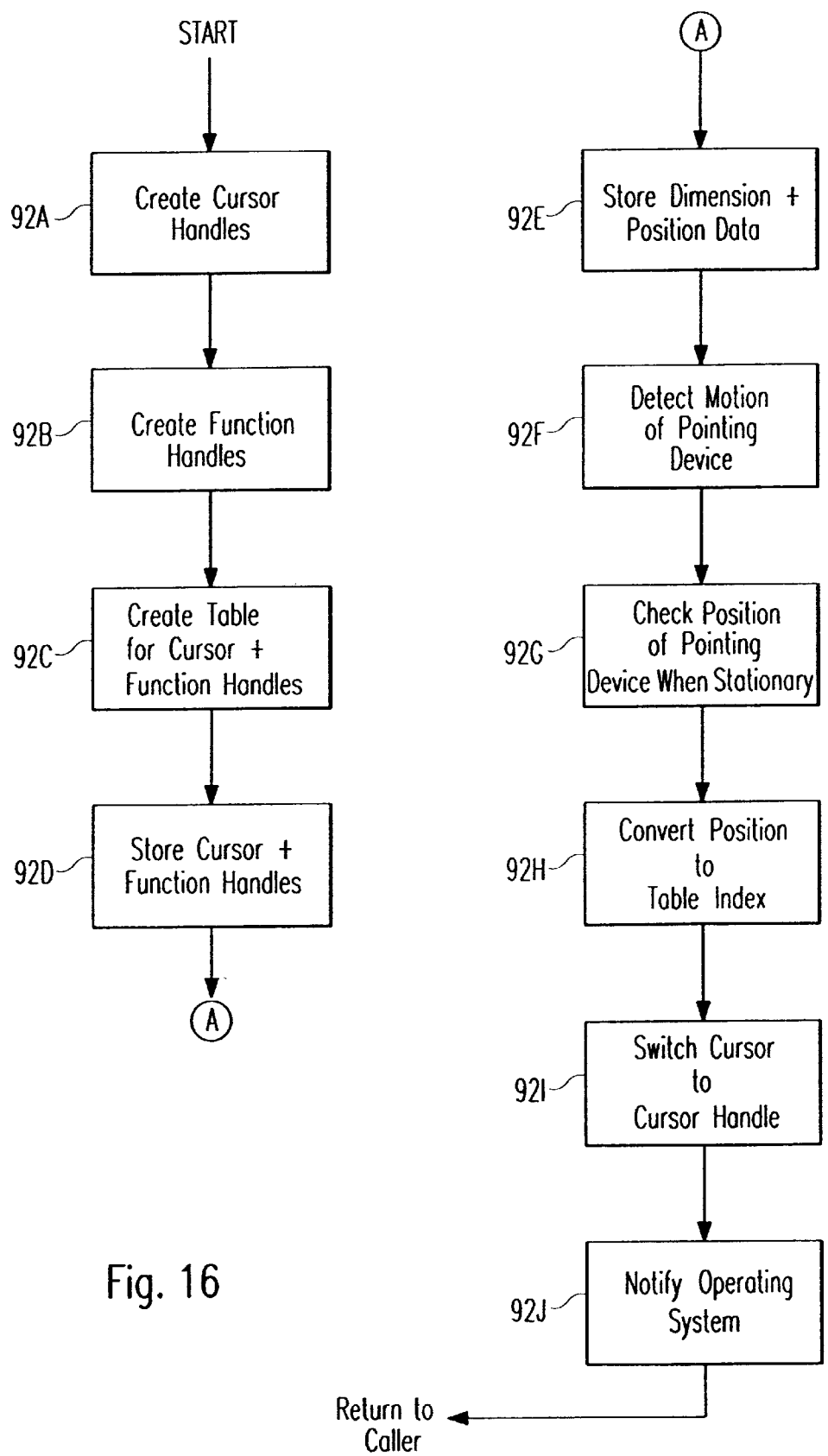
FIG. 16 is a method used by the computer program of FIG. 14 for mapping various image manipulation functions to a plurality of virtual spaces according to a preferred embodiment of the present invention.

FIG. 16 shows a method used by the ImageChildWin objects of the computer program of FIG. 14 to map a user interface command to a virtual space and subsequently to the corresponding image manipulation functions. The method includes: creating one or more cursor handles for cursors to be used in one or more image display windows (Step 92A); creating one or more function handles corresponding to one or more virtual spaces of the image display windows (Step 92B); creating a table in computer random access memory for storing the cursor handles, function handles and other data associated with the image display windows (Step 92C); storing the cursor and function handles in the table (Step 92D); storing dimension and position data associated with the virtual spaces in the table (Step 92E); detecting motion of a pointing device (Step 92F); checking the position of the pointing device after the pointing device has been stationary for a pre-determined period (Step 92G); converting the position of the pointing device into an index of the table (Step 92H); switching the cursor to the cursor handle found in the table (Step 92I); and notifying a computer operating system that a new cursor handle has been created (Step 92J).

The step of creating a table in computer random access memory ("RAM"), Step 92C, involves storing function handles for the various events 88A through 88H corresponding to the user commands and mouse movements 86A through 86H shown in FIG. 15. The step of storing the function handles further includes initializing a function table with entries corresponding to user commands and mouse movements 86A through 86H, e.g., mouse movement, a left mouse button click, a right mouse button click, a left mouse button double click, a right mouse button double click, a middle mouse button click, a combination of mouse movement and a left mouse button click, a combination of mouse movement and a right mouse button click, a middle mouse button click, etc. The function pointers for the various events 88A through 88H are then loaded into RAM and stored in the function table. The user command/mouse movement entries in the function table are then indexed by constant values returned by the operating system kernel when the corresponding event is invoked.

The events 88A through 88H shown in FIG. 15 are all processed in a similar manner, as described herein for a left mouse button click 86B. When a left mouse button click 86B is detected by the operating system, the corresponding event 88B is passed to the ImageChildWin::WndProc event handler function 91. A look-up operation is then performed on the corresponding image manipulation function to be executed in the function table. The ImageChildWin::WndProc event handler function 91 then acquires a pointer to the image manipulation function and the image manipulation function is executed.

Thus, we have described novel methods and systems for direct manipulation of digital images on one or more image display monitors.

Although the present invention has been described in connection with particular embodiments thereof, it is to be understood that such embodiments are susceptible of modification and variation without departing from the inventive concept disclosed. All such modifications and variations, therefore, are intended to be included within the spirit and scope of the appended claims.

We claim:

1. A computerized image manipulation system comprising,
   (a) a monitor;
   (b) a CPU with memory;
   (c) a user interface including:
      (i) a cursor maneuvering tool, and
      (i) user indicators associated with the cursor maneuvering tool for indicating an action associated with a location of a cursor on a display on the monitor; and (d) a program in said memory including:
  (i) programming to produce digital images on the monitor,
  (ii) programming to partition the digital images into virtual spaces occupying locations shared by portions of the digital images, and
  (iii) programming assigning image manipulation action to the partitioned virtual spaces under control of the cursor maneuvering tool and at least one of the user indicators upon movement of the cursor into a location on the image corresponding to one of the virtual spaces partitioned thereon, wherein the programming to partition the digital images into virtual spaces comprises programming that partitions at least substantially the entire image area into virtual spaces.

* * * * *

UNITED STATES PATENT AND TRADEMARK OFFICE
CERTIFICATE OF CORRECTION

PATENT NO.    : 6,509,915 B2
DATED         : January 21, 2003
INVENTOR(S)   : P M. Berman et al.

It is certified that error appears in the above-identified patent and that said Letters Patent is hereby corrected as shown below:

<u>Title page,</u>
Item [62], Related U.S. Application Data, Please replace the text "filed on Oct. 7" with the following corrected text -- filed on Nov. 7 --

Signed and Sealed this

Twenty-second Day of July, 2003

JAMES E. ROGAN
*Director of the United States Patent and Trademark Office*